United States Patent
Lee et al.

(10) Patent No.: US 10,555,965 B2
(45) Date of Patent: Feb. 11, 2020

(54) ENVIRONMENT-RESPONSIVE HYALURONIC ACID NANOPARTICLES

(71) Applicant: Industry-University Cooperation Foundation Hanyang University, Seoul (KR)

(72) Inventors: Kuen Yong Lee, Seoul (KR); Minyoung Jo, Suwon-si (KR)

(73) Assignee: Industry-University Cooperation Foundation Hanyang University, Seongdong-gu, Seoul (KR)

( * ) Notice: Subject to any disclaimer, the term of this patent is extended or adjusted under 35 U.S.C. 154(b) by 42 days.

(21) Appl. No.: 16/065,505

(22) PCT Filed: Dec. 23, 2016

(86) PCT No.: PCT/KR2016/015179
§ 371 (c)(1),
(2) Date: Jun. 22, 2018

(87) PCT Pub. No.: WO2017/111536
PCT Pub. Date: Jun. 29, 2017

(65) Prior Publication Data
US 2018/0369276 A1    Dec. 27, 2018

(30) Foreign Application Priority Data
Dec. 24, 2015    (KR) .................. 10-2015-0186691

(51) Int. Cl.
| | |
|---|---|
| A61K 9/18 | (2006.01) |
| A61K 31/728 | (2006.01) |
| G01N 33/66 | (2006.01) |
| A61K 47/69 | (2017.01) |
| A61K 47/54 | (2017.01) |
| A61P 35/00 | (2006.01) |
| A61K 47/18 | (2017.01) |
| G01N 33/58 | (2006.01) |
| B82Y 5/00 | (2011.01) |

(52) U.S. Cl.
CPC ............ *A61K 31/728* (2013.01); *A61K 47/18* (2013.01); *A61K 47/541* (2017.08); *A61K 47/6929* (2017.08); *A61P 35/00* (2018.01); *G01N 33/582* (2013.01); *G01N 33/66* (2013.01); *B82Y 5/00* (2013.01)

(58) Field of Classification Search
None
See application file for complete search history.

(56) References Cited

U.S. PATENT DOCUMENTS 9,549,987 B2 * 1/2017 Auzely-Velty ......... A61K 38/28
2015/0283247 A1 10/2015 Auzely-Velty et al.

OTHER PUBLICATIONS

Zhongming Wu et al., "Phenylboronic Acid Grafted Chitosan as a Glucose-Sensitive Vehicle for Controlled Insulin Release", Journal of Pharmaceutical Sciences, May 2011, pp. 2278-2286, vol. 100, No. 6.
Dominte Tarus et al., "Readily Prepared Dynamic Hydrogels by Combining Phenyl Boronic Acid- and Maltose-Modified Anionic Polysaccharides at Neutral pH", Macromolecular Rapid Communications, 2014, pp. 2089-2095, vol. 35.
William L. A. Brooks et al., "Synthesis and Applications of Boronic Acid-Containing Polymers: From Materials to Medicine", Chemical Reviews, 2016(Publication date: Sep. 2015), pp. 1375-1397, vol. 116.
Rujiang Ma et al., "Phenylboronic Acid-Based Complex Micelles with Enhanced Glucose-Responsiveness at Physiological pH by Complexation with Glycopolymer", Biomacromolecules, 2012, pp. 3409-3417, vol. 13.
"Development of functionalized polymeric nanoparticles for cancer diagnosis and therapy", Aug. 2013.
Internal Search Report for PCT/KR2016/015179, dated Mar. 29, 2017.

* cited by examiner

*Primary Examiner* — Susan T Tran
(74) *Attorney, Agent, or Firm* — Sughrue Mion, PLLC

(57) ABSTRACT

The present invention relates to glucose-responsive hyaluronic acid nanoparticles having boronic acid compounds chemically bonded thereto, and a composition including the same. When the nanoparticles according to the present invention are used, cancer may be diagnosed and treated using a cancer cell-specific biological mechanism, without the use of existing contrast agents and anticancer agents which have the problem of toxicity.

11 Claims, 13 Drawing Sheets
(10 of 13 Drawing Sheet(s) Filed in Color)

[Figure 3]
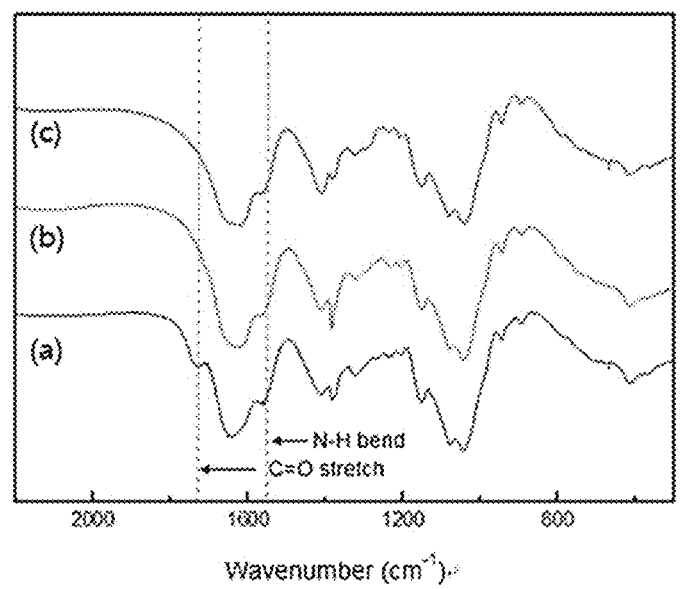
[Figure 4]
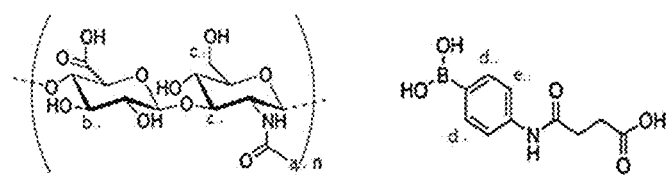
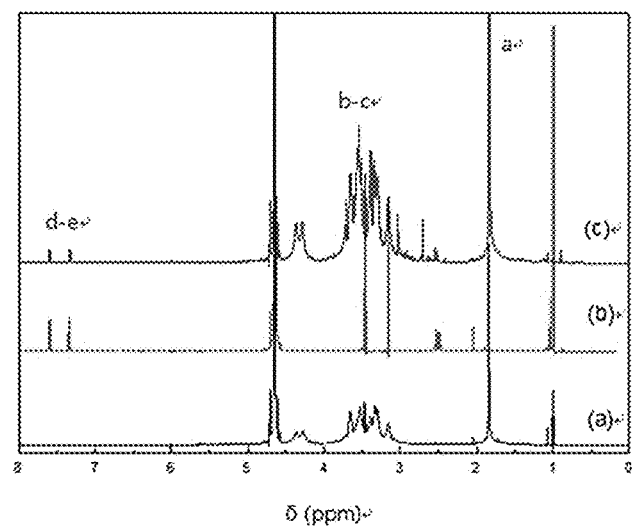

[Figure 5]
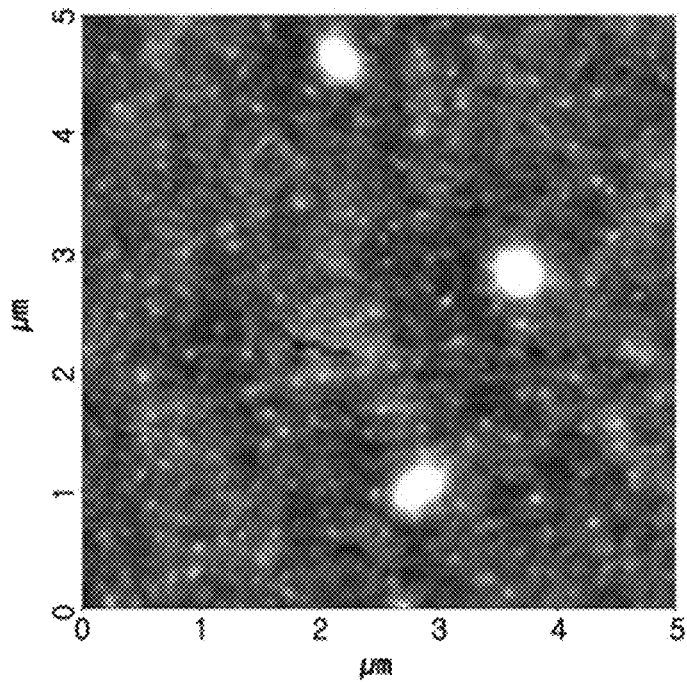
[Figure 6A]
(a)
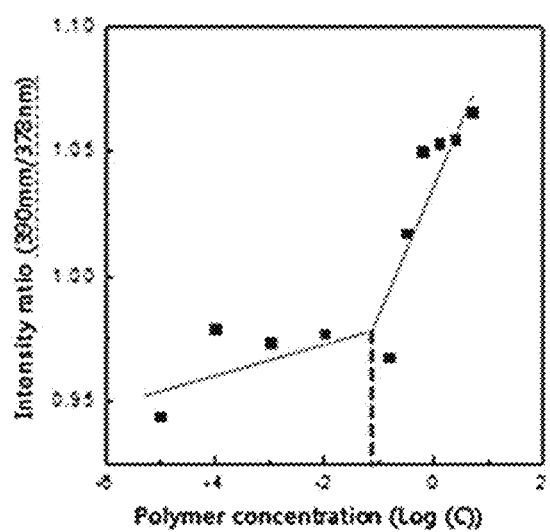

【Figure 6B】
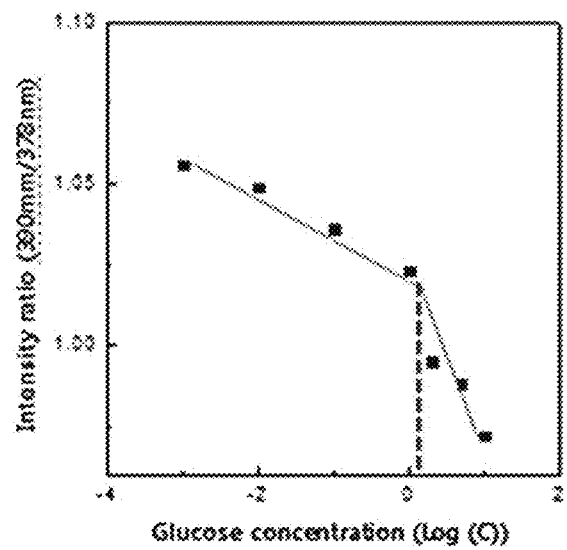
【Figure 7】
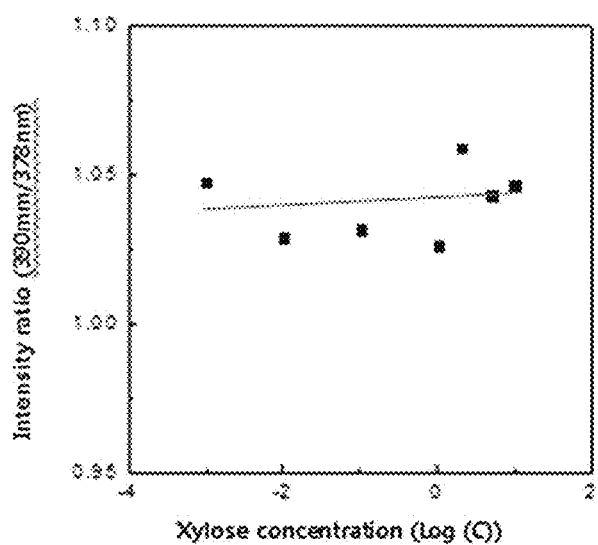

[Figure 9]
(a)
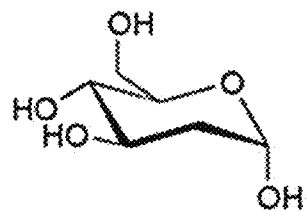
2-deoxy-D-glucose
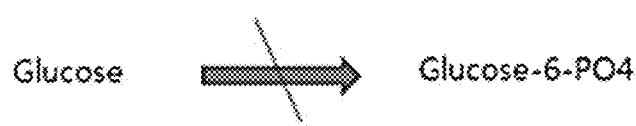
(b)
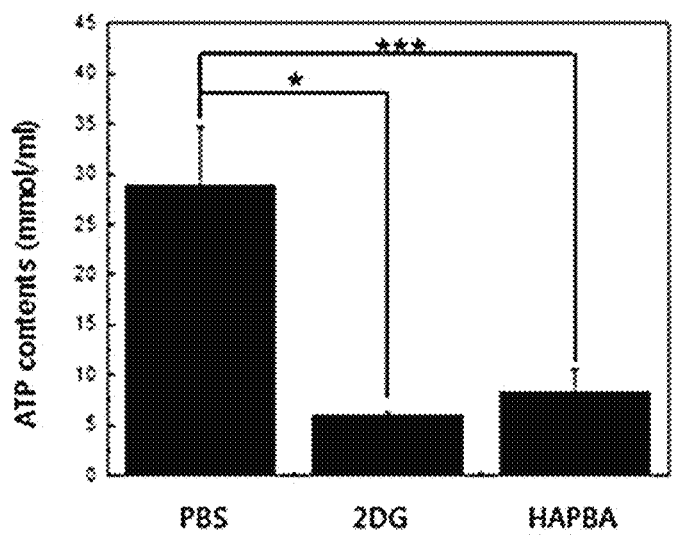

[Figure 10]
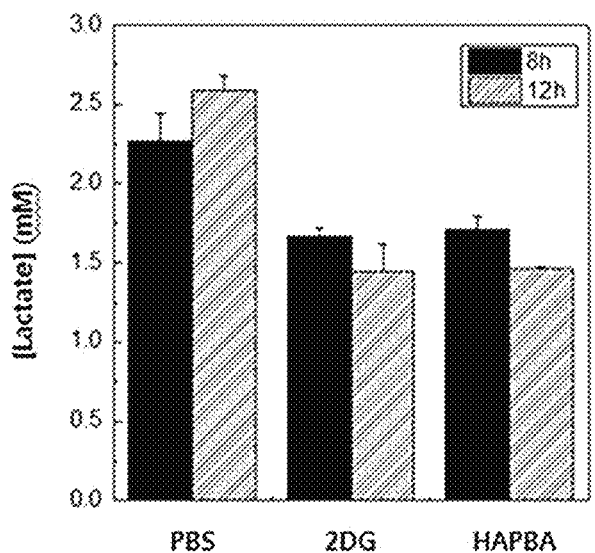
[Figure 11 a]
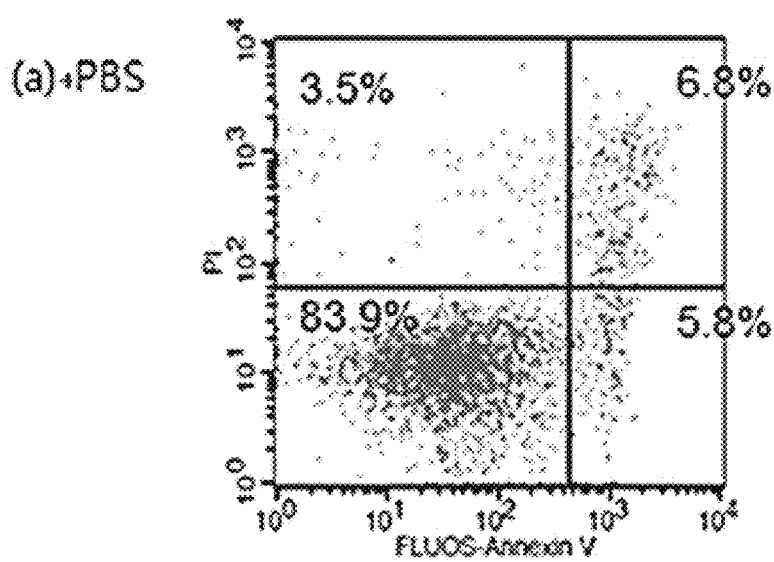

【Figure 11 b】
(b)·2DG
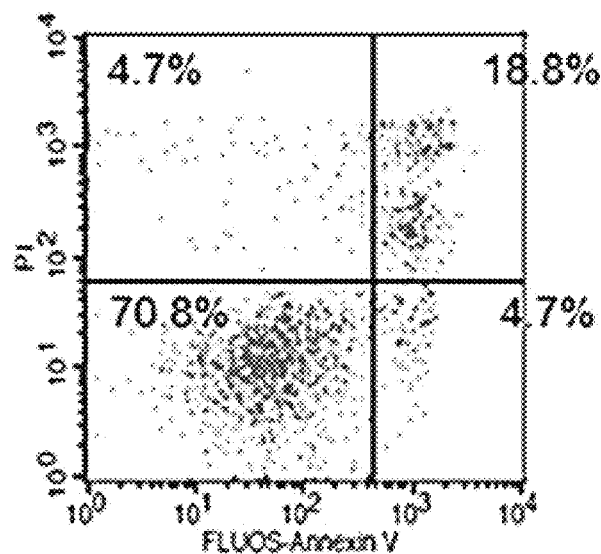
【Figure 11 c】
(c)·HAPB
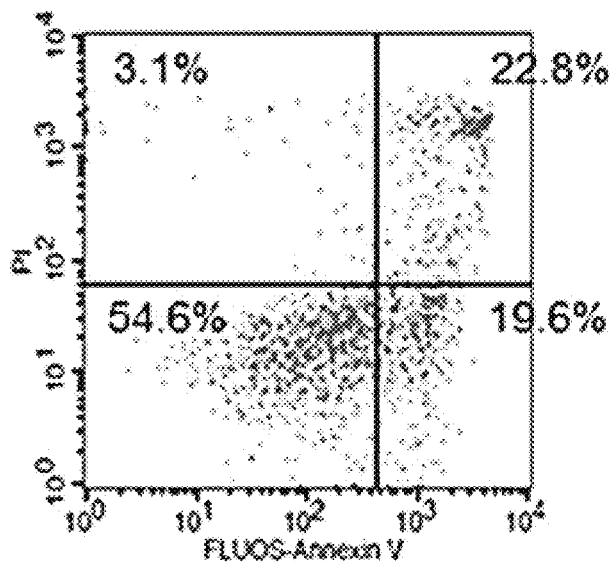

【Figure 12】
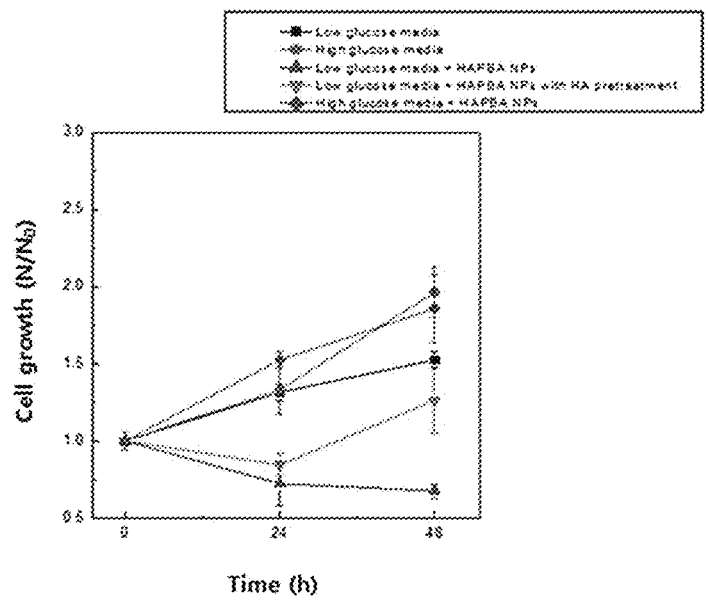
【Figure 13】
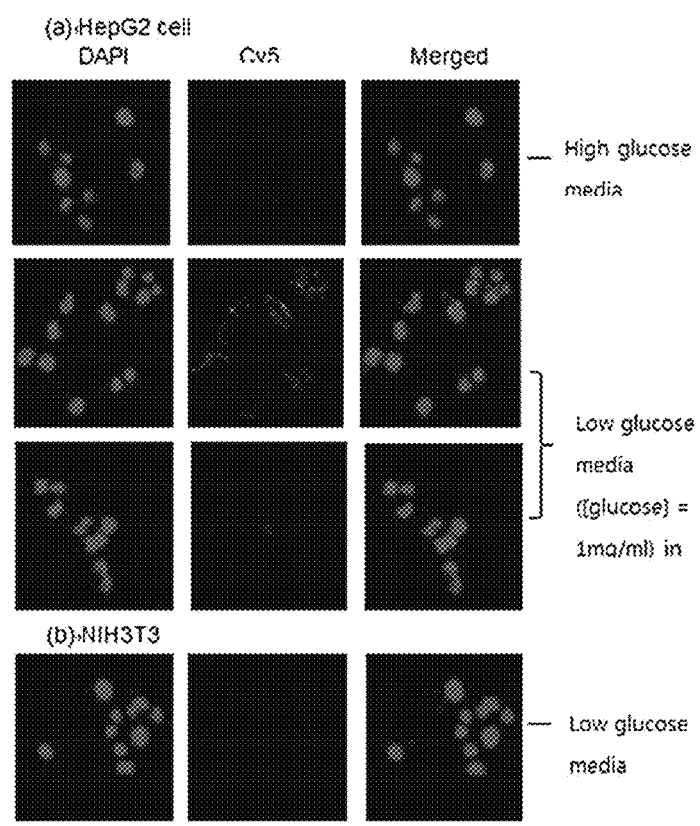

[Figure 14]
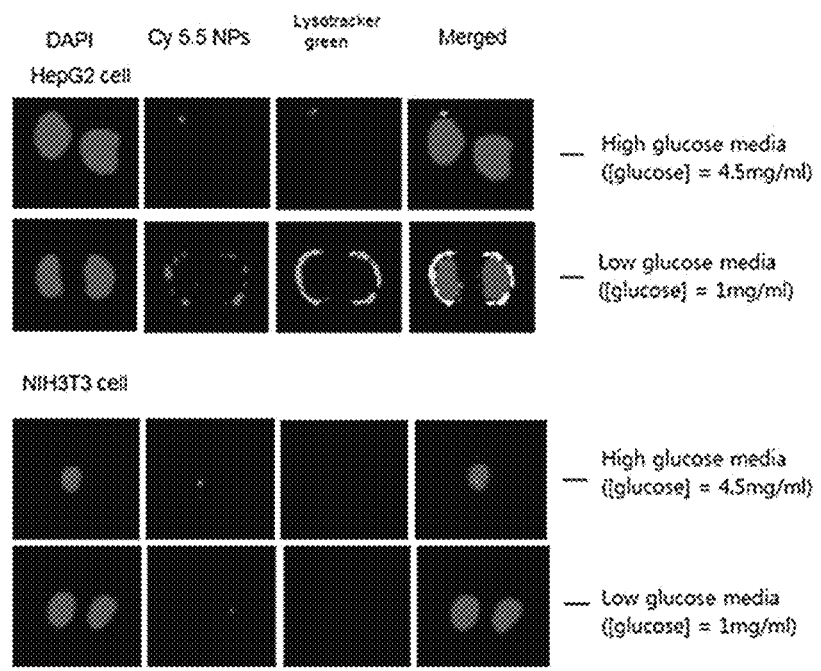

[Figure 15]
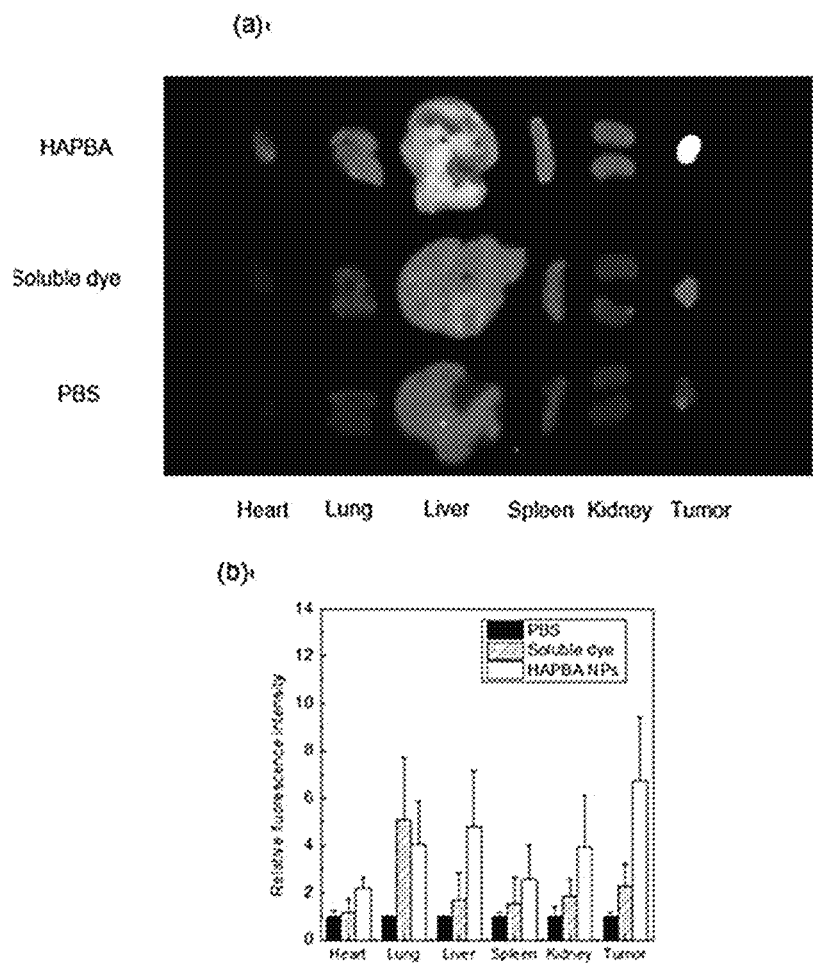

[Figure 16]
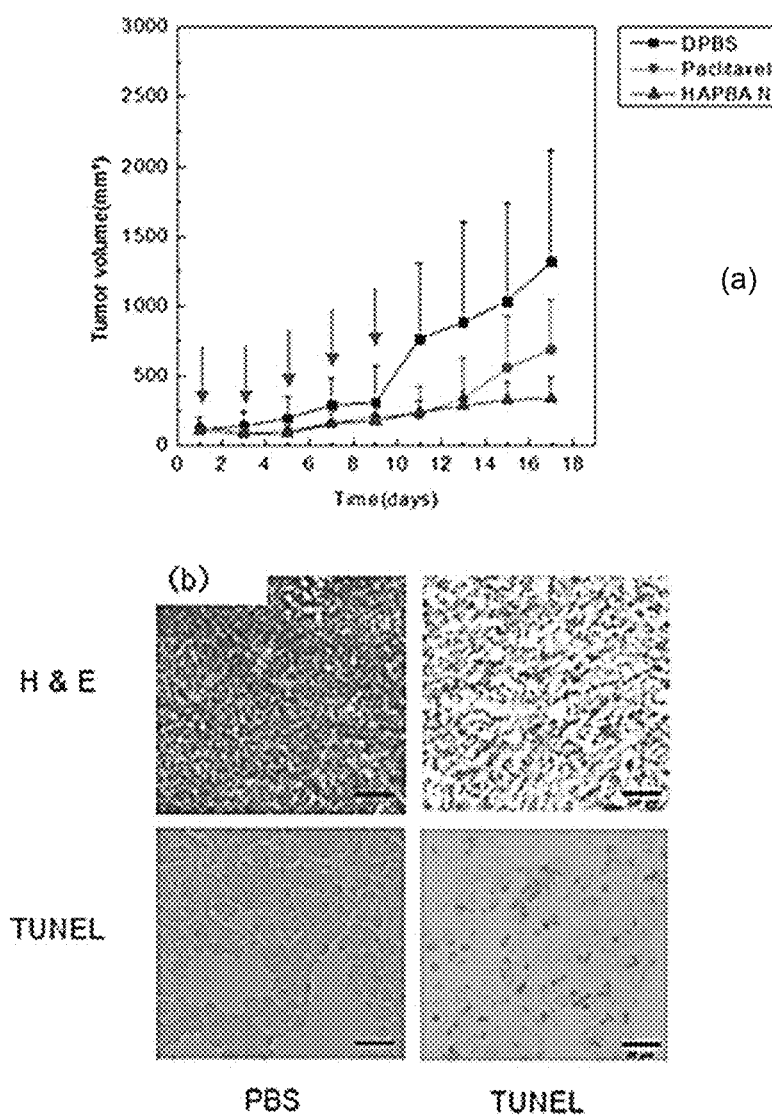

ENVIRONMENT-RESPONSIVE HYALURONIC ACID NANOPARTICLES

CROSS REFERENCE TO RELATED APPLICATIONS

This application is a National Stage of International Application No. PCT/KR2016/015179 filed Dec. 23, 2016, claiming priority based on Korean Patent Application No. 10-2015-0186691 filed Dec. 24, 2015.

TECHNICAL FIELD

The present invention relates to glucose-responsive nanoparticles in which a boronic acid compound is chemically bonded to hyaluronic acid.

BACKGROUND ART

Studies on treatment of diabetes using materials having glucose-responsive characteristics have been conducted. Up to date, polymeric composites using phenylboronic acid have been widely used to treat diabetes, and methods using the composites as drug delivery systems have been developed. Also, studies on cancer treatment using biocompatible polymer nanoparticles have been actively conducted. However, most studies have side effects of destroying normal cells as well as cancer cells.

Research on cancer-specific delivery of contrast agents and anticancer agents having potential toxicity using biocompatible materials has been actively conducted. In recent years, the research paradigm for 'theragnosis' has come into the spotlight as one of the fusion techniques enabling simultaneous diagnosis and therapy [Ryu J et al., "Tumor-targeting multi-functional nanoparticles for theragnosis: New paradigm for cancer therapy," Advanced Drug Delivery Reviews 64: 1447-1458 183-192(Jul. 4, 2012)]. Cancer cells have a Warburg effect in which the cancer cells inefficiently produce energy, compared to the normal cells. This abnormal glycolysis results in the uptake of a high concentration of glucose into the cancer cells [Reuben J S, "Glucose metabolism and cancer", Current Opinion in Cell Biology 18: 598-608 (Oct. 12, 2006); Robert A G et al., "Why do cancer have high aerobic glycolysis", Nature Review 4: 891-899 (November 2004)]. Examples of diagnosis of cancers using the unique biological mechanism of such cancer cells have been reported. However, no application to simultaneous cancer diagnosis and therapy through the regulation of cell metabolism has been reported yet.

On the other hand, it has been reported that hydrophobic phenylalanine-based compounds specifically bind to glucose to lose their hydrophobic property [Shull B et al., "P-Boronophenylalanine complexes with fructose and related carbohydrates and polyols", U.S. Pat. No. 6,169,076 B1 (Jan. 2, 2001)]. There are reports on the application of this phenomenon to treatment of diabetes [Kataoka, K, et al. "Totally synthetic polymer gels responding to external glucose concentration: Their preparation and application to on-off regulation of insulin release." Journal of the American Chemical Society 120: 12694-12695 (November 1998)]. However, no application of such a phenomenon to simultaneous cancer diagnosis and therapy has been reported yet.

As the prior art for diagnosis and treatment of diseases, target-directed probes, contrast agents, and biocompatible delivery systems including a therapeutic agent have been widely used. In particular, many polymer nanoparticles that can be used to simultaneously diagnose and treat cancer have been developed. However, most of the contrast agents used for simultaneous diagnosis and treatment of cancer have potential toxicity problems, which have been raised so far, such as kidney toxicity and exposure to radiation. Also, the uncontrollable risk caused by non-specific delivery of the anticancer agents has become a leading cause of limiting the therapy using the anticancer agents to ancillary therapeutic methods in the field of clinical trials.

Throughout this application, many publications and patents are referenced and the citations thereof are provided in parentheses. The disclosures of these publications and patents are hereby incorporated by reference in their entities into this application in order to fully describe the present invention and the state of the art to which the present invention pertains.

DISCLOSURE

Technical Problem

The present inventors have endeavored to develop a composition for cancer cell-specific diagnosis and/or therapy using a cancer-specific biological mechanism without using conventional contrast agents and anticancer agents having toxicity problems.

Accordingly, the present inventors have found that glucose-responsive nanoparticles, in which a boronic acid compound is bound to hyaluronic acid, are selectively delivered to cancer tissues, especially liver cancer tissues, due to an enhanced permeability and retention (EPR) effect. Also, the present inventors have established that the boronic acid compound binds to glucose to visualize the cancer tissues and induce energy deficiency in cancer cells. Therefore, the present invention has been completed based on these facts.

Particularly, because the hyaluronic acid has a characteristic of binding to a CD44 receptor in the cancer cells, the cancer-specific delivery of the nanoparticles using the hyaluronic acid is possible.

Therefore, an aspect of the present invention is to provide glucose-responsive nanoparticles.

Another aspect of the present invention is to provide a composition for diagnosing or treating liver cancer or simultaneously diagnosing and treating liver cancer.

Other purposes and advantages of the present invention will become more obvious with the following detailed description of the present invention, the claims, and the accompanying drawings.

Technical Solution

The present invention provides a hyaluronic acid complex including a hyaluronic acid-boronic acid repeating unit in which a boronic acid compound is bound to a carboxyl group of a repeating unit represented by the following Formula 1.

[Formula 1]

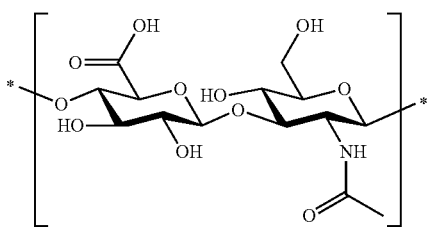

Also, the present invention provides glucose-responsive nanoparticles that are spherical particles having a hydrophobic core, wherein the aforementioned hyaluronic acid complex is self-aggregated to form the spherical particles.

Also, the present invention provides a method of preparing a hyaluronic acid complex, which includes allowing a boronic acid compound to react with hyaluronic acid to prepare a hyaluronic acid complex.

Also, the present invention provides a method of preparing glucose-responsive nanoparticles, which includes dispersing the aforementioned hyaluronic acid complex in an aqueous solution to self-aggregate the hyaluronic acid complex in order to prepare spherical particles having a hydrophobic core.

Also, the present invention provides a pharmaceutical composition for diagnosing or treating liver cancer, which includes the aforementioned glucose-responsive nanoparticles.

Advantageous Effects

In summary characteristics and advantages of the present invention are as follows:

(a) The present invention provides the glucose-responsive nanoparticles.

(b) The present invention provides the composition for diagnosing or treating liver cancer or simultaneously diagnosing and treating liver cancer.

(c) When the nanoparticles of the present invention are used, cancer can be diagnosed and treated using a cancer cell-specific biological mechanism without using the conventional contrast agents and anticancer agents having toxicity problems.

(d) When the nanoparticles of the present invention are used, the nanoparticles can be selectively delivered to cancer tissues and visualized, and energy deficiency in cancer cells can be induced to treat cancer.

(e) When the nanoparticles of the present invention are used, cancer can be treated by cutting off energy metabolic pathways without having a direct impact on cells.

DESCRIPTION OF DRAWINGS

The patent or application file contains at least one drawing executed in color. Copies of this patent or patent application publication with color drawings will be provided by the Office upon request and payment of the necessary fee.

FIG. 3 shows the results of FT-IR analyses of hyaluronic acid and the hyaluronic acid complex.

FIG. 4 shows the results of 1H-NMR analysis of hyaluronic acid, the boronic acid compound and glucose-responsive nanoparticles.

FIG. 5 shows an AFM image for identifying the morphology of the glucose-responsive nanoparticles.

FIGS. 6A and 6B show the results of measuring a critical micelle concentration (CMC) of the nanoparticles to determine a micelle-forming concentration of the hyaluronic acid complex.

FIG. 7 shows the results of measuring the pyrene excitation spectra of the glucose-responsive nanoparticles in the presence of a varying concentration of xylose.

FIG. 9 shows (A) a chemical structure of 2-deoxy-D-glucose and (B) in vitro ATP contents of HepG2 cells.

FIG. 10 shows in vitro secretion of lactate in the HepG2 cells.

FIGS. 11A, 11B and 11C show the results of determining apoptosis and necrosis in the HepG2 cells using flow cytometry.

FIG. 12 show the results of growth of HepG2 cells treated daily with a low glucose medium, a high glucose medium, a low glucose medium including the nanoparticles, a high glucose medium including the nanoparticles, and a HA-pretreated low glucose medium including the nanoparticles.

FIG. 13 shows a confocal microscopy image of (A) HepG2 cells and (B) NIH3T3 cells treated with Cy5.5-conjugated HA-PBA nanoparticles in the low glucose medium or the high glucose medium.

FIG. 14 shows cellular entry of the Cy5.5-conjugated HA-PBA nanoparticles in the low and high glucose media.

FIG. 15 shows (A) an in vivo biodistribution of the nanoparticles and (B) the results of quantifying tumor specificity in a tumor-bearing mouse model.

FIG. 16 shows (A) the results of in vivo therapeutic efficacy of the nanoparticles and (B) the results of H&E and TUNEL staining of tumor tissues.

BEST MODEL

Figure 1:
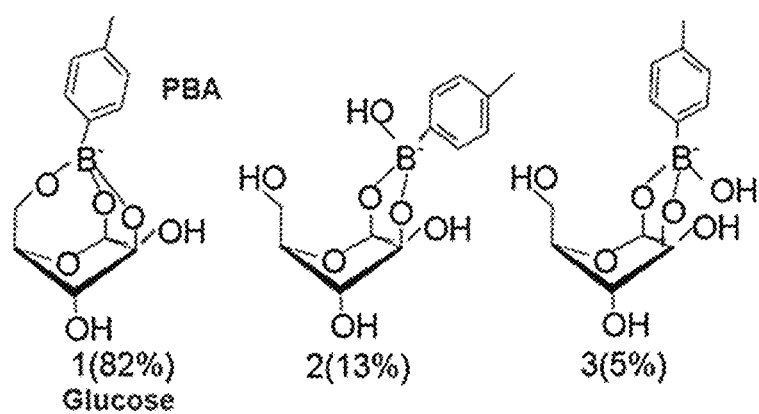
FIG. 1 shows three types of boronic acid compounds binding to glucose.

The present inventors have endeavored to develop a composition for cancer cell-specific diagnosis, therapy or simultaneous cancer-specific diagnosis and therapy using a cancer-specific biological mechanism without using conventional contrast agents and anticancer agents having toxicity problems.

Accordingly, the present inventors have established that, when glucose-responsive nanoparticles, in which a boronic acid compound is bound to hyaluronic acid, are used, the glucose-responsive nanoparticles are selectively delivered to cancer tissues due to an enhanced permeability and retention (EPR) effect, and bind to glucose to visualize the cancer tissues and induce energy deficiency in cancer cells.

Hereinafter, the present invention will be described in further detail.

The present invention is directed to a hyaluronic acid complex including a hyaluronic acid-boronic acid repeating unit in which a boronic acid compound is bound to a carboxyl group of a repeating unit represented by the following Formula 1.

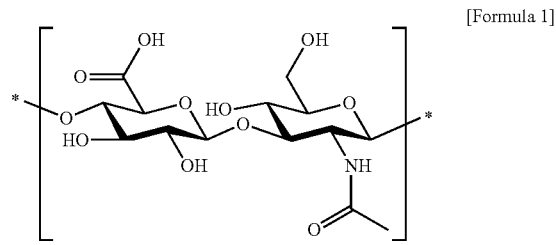

[Formula 1]

The repeating unit represented by Formula 1 may be referred to as a repeating unit of Formula 1.

In the present invention, the term "repeating unit" refers to a structural unit that is minimally repeated in a polymer.

For example, when a repeating unit in a linear polymer is indicated by 'M,' the structure of the polymer may be indicated by '-[M]n-.'

The hyaluronic acid complex of the present invention may include a hyaluronic acid-boronic acid repeating unit as the repeating unit. In the present invention, the hyaluronic acid complex may include a hyaluronic acid repeating unit represented by Formula 1 together with the hyaluronic acid-boronic acid repeating unit. The two types of the repeating units are arranged in a regular or irregular sequence.

A content of the hyaluronic acid-boronic acid repeating unit may be in a range of 15 to 55 parts by mol, 18 to 40 parts by mol, or 20 to 35 parts by mol, based on 100 parts by mol of the hyaluronic acid complex.

In the hyaluronic acid-boronic acid repeating unit of the present invention, phenylboronic acid may be used as the boronic acid compound. In this case, one or more selected from the group consisting of N-(4-phenylboronic) succinamic acid, 3-carboxybenzenebenzoic acid, 4-carboxypyridine-3-benzoic acid, and (3-aminomethylphenyl) benzoic acid chloride may be used as the phenylboronic acid.

The boronic acid compound may be bound to the hyaluronic acid repeating unit via an amide bond. Specifically, the carboxyl group of hyaluronic acid may react with an amine group of the boronic acid compound to form an amide bond.

In this case, (3-aminomethylphenyl) benzoic acid chloride may be used as the boronic acid compound.

Also, the boronic acid compound may be bound to the hyaluronic acid repeating unit via the amide bond by means of a diamine compound serving as a linker. Specifically, a carboxyl group of the hyaluronic acid may form an amide bond with an amine group of the diamine compound, and an amine group which does not form a bond in the diamine compound may form an amide bond with a carboxyl group of the boronic acid compound.

In this case, one or more selected from the group consisting of N-(4-phenylboronic) succinamic acid, 3-carboxybenzenebenzoic acid, and 4-carboxypyridine-3-benzoic acid may be used as the boronic acid compound.

Also, ethylenediamine, butylenediamine, hexamethylenediamine, pentaethylenehexamine, or 1,5-diamino-2-methylpentane may be used as the diamine compound.

The hyaluronic acid complex of the present invention may have a molecular weight of 50 to 500 kDa or 200 to 300 kDa.

In the hyaluronic acid complex of the present invention, hyaluronic acid moieties of the hyaluronic acid repeating unit and the hyaluronic acid-boronic acid repeating unit have a hydrophilic property, and a boronic acid moiety of the hyaluronic acid-boronic acid repeating unit has a hydrophobic property. That is, the hyaluronic acid complex is an amphipathic polymer including both a hydrophilic moiety and a hydrophobic moiety.

Also, the present invention is directed to a self-aggregate of the aforementioned hyaluronic acid complex. The hyaluronic acid complex is self-aggregated to form spherical particles having a hydrophobic core. In this case, a spherical shape may include circular and oval shapes. The spherical particles may be referred to as the nanoparticles. In this case, because the nanoparticles have glucose responsivity, the nanoparticles may be referred to as glucose-responsive nanoparticles.

The hyaluronic acid complex of the present invention has an amphipathic property. In this case, a boronic acid moiety having a hydrophobic property may form a plurality of inner cores to form stable spherical particles. Such a spherical shape allows a particle structure to be stably maintained under a general in vivo glucose environment, and the particle structure is not maintained under a specific high-concentration glucose environment in cancer tissues. Therefore, the glucose-responsive nanoparticles introduced into cancer cells collect glucose to effectively inhibit aerobic glycolysis and suppress cancer growth. An anti-glycolytic mechanism of the glucose-responsive nanoparticles through glucose collection does not have a direct impact on normal cells. This may solve the potential toxicity problems of the nanoparticles, which have been restricted to the role as a delivery system for conventional anticancer drugs or contrast agents.

The average particle diameter of the glucose-responsive nanoparticles according to the present invention is not particularly limited. For example, the particle diameter may be in a range of 200 to 400 nm, or 200 to 300 nm. Generally, as the content of the hyaluronic acid-boronic acid repeating unit becomes higher, the average diameter of the nanoparticles tends to become smaller due to a packing effect.

The glucose-responsive nanoparticles according to the present invention may further include a fluorescent signal material which is chemically labeled on the spherical particles or is physically loaded into the hydrophobic cores. The fluorescent signal material may be used to apply the nanoparticles to targeted diagnosis of various cancers.

The term "chemical labeling" refers to chemical binding (e.g., covalent bonding) through which a fluorescent signal material is introduced into the nanoparticles. In the case of the chemical labeling, the fluorescent signal material does not need to be necessarily formed inside the hydrophobic cores.

For example, the fluorescent signal material that may be used herein may include fluorescent organic materials such as chlorine 6 (Ce6), the cyanine dye series (Cy3, Cy5, or Cy5.5), fluorescein and derivatives thereof, rhodamine and derivatives thereof, Lucifer Yellow, B-phytoerithrin, 9-acridineisothiocyanate, Lucifer Yellow VS, 4-acetamido-4'-isothiocyanatostilbene-2,2'-disulfonic acid, 7-diethylamino-3-(4'-isothiocyatophenyl)-4-methylcoumarin, succinimidyl-pyrenebutyrate, 4-acetamido-4'-isothiocyanatostilbene-2,2'-disulfonic acid derivatives, LCTM-Red 640, LCTM-Red 705, the Alexa dye series, the Lissamine series, isothiocyanate, erythrosine isothiocyanate, diethylenetriamine pentaacetate, 1-diethylamino naphthyl-5-sulfonate, 1-anilino-8-naphthalene sulfonate, 2-p-touidinyl-6-naphthalene sulfonate, 3-phenyl-7-isocyanatocoumarin, 9-isothiocyanatoacridine, Acridine Orange, N-(p-(2-benzoxazolyl)phenyl) maleimide, benzoxadiazole, stilbene, and pyrene; and inorganic fluorescent semiconductor nanoparticles (quantum dots).

Also, the present invention is directed to a method of preparing the aforementioned hyaluronic acid complex.

The hyaluronic acid complex may be prepared by allowing a boronic acid compound to react with hyaluronic acid.

The hyaluronic acid is a natural polymer that exhibits excellent biocompatibility and has low toxicity and poor immunogenicity like hyaluronic acid naturally existing in the extracellular matrix. Also, the hyaluronic acid has a characteristic of binding to a CD44-receptor in cancer cells. The in vivo cancer-specific delivery of the nanoparticles using the characteristic is possible.

The hyaluronic acid may have a molecular weight of 50 to 500 kDa, or 200 to 300 kDa. The molecular weight of the hyaluronic acid is associated with the length of the chain of a hyaluronic acid polymer to be prepared, which has an influence on the diameter of the glucose-responsive nanoparticles. In the present invention, the molecular weight of the hyaluronic acid is selected in this point of view The hyaluronic acid may be used in the form of a hyaluronate. Sodium hyaluronate may be used as the hyaluronate. In one exemplary embodiment of the present invention, the hyaluronic acid and hyaluronate may be generally referred to as 'HA.'

In the present invention, the method may further include allowing a diamine compound to react with the hyaluronic acid to modify the hyaluronic acid prior to allowing the boronic acid compound to react with the hyaluronic acid.

Hereinafter, the modified hyaluronic acid may be referred to as modified hyaluronic acid or hyaluronic acid derivatives.

The aforementioned components may be used as the diamine compound.

The diamine compound has two amine groups: one amine group may form a bond with hyaluronic acid, and the other amine group may form a bond with a boronic acid compound as will be described below. That is, the diamine compound may serve as a linker to bind the boronic acid compound to hyaluronic acid.

Specifically, in this step, the hyaluronic acid and the diamine compound are reacted to form an amine group (—NH2) in the hyaluronic acid. The reaction may be carried out through an EDC/NHS reaction (Bartczak. D, Kanaras A. G, Preparation of peptide-functionalized gold nanoparticles using one pot EDC/Sulfo-NHS coupling. Langmuir 2011; 27:10119-10123). The formation of the amine group in the hyaluronic acid is not realized in all repeating units of hyaluronic acid, that is, repeating units in which D-glucuronic acid and D-N-acetylglucosamine are linked via glycosidic bonds.

In the present invention, the hyaluronic acid or modified hyaluronic acid reacts with the boronic acid compound to form a hyaluronic acid complex. The hyaluronic acid complex includes the hyaluronic acid-boronic acid repeating unit in which the boronic acid compound is bound to the carboxyl group of the repeating unit of Formula 1, as described above. Also, the complex of the present invention may include a hyaluronic acid repeating unit together with the hyaluronic acid-boronic acid repeating unit.

In the present invention, the boronic acid compound forms a bond with glucose, as shown in FIG. 1. In this way, the glucose may inhibit glycolysis and suppress cancer growth.

The aforementioned types of boronic acid compounds may be used as the boronic acid compound of the present invention.

According to one exemplary embodiment, the boronic acid compound may have the following structure.

[Formula 2]

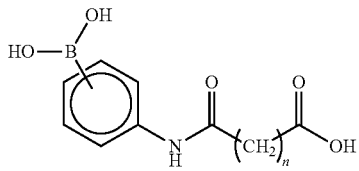

In Formula 2, a dihydroxyboronyl group and an amide group may be located at an ortho (o), meta (m), or para (p) position, preferably a para (p) position with respect to each other. Also, n may be an integer ranging from 1 to 5, or an integer ranging from 2 to 3.

According to one exemplary embodiment of the present invention, N-(4-phenylboronic) succinamic acid may be used as the boronic acid compound. However, this is just one exemplary embodiment of the present invention, an ability of the nanoparticles of the present invention to collect glucose is determined based on the presence of a boronic acid group, as shown in FIG. 1. Therefore, the N-(4-phenylboronic) succinamic acid is not necessarily used herein.

In the present invention, the bond is formed through reaction of the boronic acid compound with the hyaluronic acid or modified hyaluronic acid. Such a bond refers to a chemical bond between the hyaluronic acid or modified hyaluronic acid and the boronic acid compound. The bond may be an amide bond formed between a carboxyl group and an amine group.

In the present invention, a degree of substitution (DS) of the boronic acid compound bound to the hyaluronic acid or modified hyaluronic acid may be in a range of 15 to 55, 18 to 40, or 20 to 35. The degree of substitution of the boronic acid compound is defined as the number of repeating units of hyaluronic acid, that is, the number of repeating units to which the boronic acid compound is bound per 100 repeating units in which D-glucuronic acid and D-N-acetylglucosamine are linked via a glycosidic bond. When a complex having a degree of substitution of 15 or more is prepared, structural stability of the prepared complex may be maintained, and it is difficult and inefficient for a complex having a degree of substitution of greater than 55 to form the nanoparticles. In the hyaluronic acid complex prepared to have the degree of substitution, the content of the hyaluronic acid-boronic acid repeating unit is in a range of 15 to 55 parts by mol, based on 100 parts by mol of the hyaluronic acid complex.

Also, in the present invention, the method includes self-aggregating the hyaluronic acid complex to form spherical particles.

When the hyaluronic acid complex is dispersed in an aqueous solution, for example, distilled water, the complex is spontaneously self-aggregated to form spherical particles having a plurality of hydrophobic cores. The hyaluronic acid complex of the present invention has an amphipathic property. In this case, a boronic acid moiety having a hydrophobic property may form a plurality of inner cores, thereby forming stable spherical particles. This spherical shape allows a particle structure to be maintained under a general in vivo glucose environment, and the particle structure is responsive under a specific high-concentration glucose environment in cancer tissues.

Also, in the present invention, the method may further include labeling the glucose-responsive nanoparticles with a fluorescent signal material, or loading the hydrophobic cores with the fluorescent signal material.

The aforementioned types of fluorescent signal materials may be used as the fluorescent signal material without limitation. Also, the labeling or loading with the fluorescent signal material may be carried out using conventional methods known in the related art.

Also, the present invention is directed to a composition including the glucose-responsive nanoparticles.

The composition may be used to diagnose or treat liver cancer, and may be used to simultaneously diagnose and treat liver cancer.

The composition of the present invention inhibits the aerobic glycolytic metabolism of cancer cells through glucose responsivity. The glucose-responsive nanoparticles introduced into the cancer cells may collect glucose to effectively inhibit glycolysis thereof and suppress cancer growth. Particularly, the inhibition of glycolysis by the composition of the present invention does not have a direct impact on the cells.

The composition of the present invention enables cancer tissue-specific diagnosis through the glucose responsivity. The composition of the present invention may be selectively delivered to cancer tissues due to an enhanced permeability and retention (EPR) effect, and binds to glucose based on the glucose responsivity to visualize the cancer tissues. The composition of the present invention enables an observation of cancer cells through all methods capable of observing the in vivo behavior of polymers, which are usually known in the prior art or will be developed in the future.

In one exemplary embodiment, mixed particles of fluorescence-labeled glucose-responsive nanoparticles and a glucose-insensitive conjugate bound to a quencher (Black hole quencher-3 (BHQ-3)) are prepared, and delivered into cancer cells. As the glucose-responsive nanoparticles are selectively bound/dissociated to/from glucose in vivo, the nanoparticles may be visualized in a cancer-specific manner through a principle of recovering the fluorescent signals quenched away from an area of the quencher. The diagnostic method is not limited thereto, and other imaging methods may be used without limitation.

In addition to the glucose-responsive nanoparticles, the composition of the present invention may further include a pharmaceutically acceptable carrier as an active ingredient. The carrier is generally used upon formulation, and may include lactose, dextrose, sucrose, sorbitol, mannitol, starch, acacia gum, calcium phosphate, alginate, gelatin, calcium silicate, microcrystalline cellulose, DMSO, polyvinyl pyrrolidone, cellulose, water, syrup, methyl cellulose, methyl hydroxybenzoate, propyl hydroxybenzoate, talc, magnesium stearate, and mineral oil. The pharmaceutical composition of the present invention may further include a lubricant, a wetting agent, a sweetening agent, a flavoring agent, an emulsifying agent, a suspending agent, a preservative, and the like in addition to the aforementioned components.

The pharmaceutical composition of the present invention may be preferably parenterally administered, for example, may be administered through intravenous administration, intraperitoneal administration, intramuscular administration, subcutaneous administration, or topical administration.

According to one exemplary embodiment of the present invention, the composition of the present invention is injected into the body through topical or systemic administration into liver tissues. The glucose-responsive nanoparticles, which are the active ingredient of the composition of the present invention, have target directivity to cancer cells, particularly liver-specific delivery characteristics, and thus enables the diagnosis and therapy of liver cancer through topical or systemic administration into the liver tissues. The liver cancer of the present invention includes all malignant tumors located in liver tissues, such as intrahepatic cholangiocarcinoma, malignant tumors metastasized from other tissues and developed in liver tissues, as well as general hepatocellular carcinoma.

The appropriate dose of the pharmaceutical composition of the present invention varies depending on factors such as a preparation method, an administration mode, the age, weight and sex of a patient, the severity of symptoms of a disease, a diet, the duration of administration, a route of administration, a secretion rate, and the sensitivity to response. Generally, a skilled physician may easily determine and prescribe the dose of the composition effective for desired treatment. Meanwhile, the dose of the composition of the present invention is preferably 0.001 to 1,000 mg/kg (body weight) per day.

The pharmaceutical composition of the present invention may be formulated into unit dosage forms or multidose containers, using a pharmaceutically acceptable carrier and/or excipient according to the methods that may be easily executed by a person having ordinary skill in the art to which the present invention pertains. In this case, the dosage forms may be in the form of a solution in an oily or aqueous medium, a suspension, or an emulsion, or may also be in the form of an extract, a powder, a granule, a tablet, or a capsule, and may further include a dispersant or a stabilizer.

Mode for Invention

Hereinafter, the present invention will be described in further detail with reference to exemplary embodiments thereof. It will become apparent to those skilled in the art that these exemplary embodiments are intended to more specifically describe the present invention, and the scope of the present invention is not limited to the exemplary embodiments without departing from the gist of the present invention.

EXAMPLES

Materials

Sodium hyaluronate (HA) (MW=200 kDa) was purchased from Lifecore (USA), N-(4-phenylboronic) succinamic acid (PBA), ethylenediamine, 1-ethyl-3-(dimethylaminopropyl) carbodiimide (EDC), deuterium oxide (D2O), dimethyl sulfoxide (DMSO), deuterated dimethyl sulfoxide (DMSO-d6), glucose, xylose, 2-deoxy-D-glucose, and 3-(4,5-dimethylthiazol-2-yl)-2,5-diphenyl tetrazolium boromide (MTT) were purchased from Sigma Aldrich (USA).

Phosphate buffered saline (PBS), Dulbecco's modified Eagle's medium (DMEM), penicillin-streptomycin, trypsin-EDTA, and fetal bovine serum (FBS) were purchased from Gibco. N-hydroxysulfosuccinimide (sulfo-NHS) was purchased from Thermo Scientific. EZ-Cytox was purchased from Dogen (Korea), and doxorubicin hydrochloride was purchased from LC Laboratories (USA). Flamma 675 carboxylic acid was purchased from BioActs (Korea). Water was distilled, and deionized using a Milli-Q system. Immunodeficient mice (BALB/C nude, male, 5 week-old) were purchased from Orient Bio Inc.

Example 1

Preparation of Glucose-Responsive Nanoparticles

PBA was covalently conjugated to the backbone of hyaluronic acid (HA) by carbodiimide chemistry to prepare glucose-responsive nanoparticles. Hereinafter, the glucose-responsive nanoparticles may be referred to as HA-PBA nanoparticles or HAPBA nanoparticles.

In the present invention, the contents of the respective components may be adjusted depending on the desired degree of substitution (DS).

(1) Hyaluronic Acid Modification (Preparation of Hyaluronate-Ethylenediamine Conjugate)

Sodium hyaluronate was dissolved in an MES buffer (pH 6.5) to prepare a solution with 1% (w/w) concentration. Thereafter, ethylenediamine was added thereto, and EDC and sulfo-NHS were added to the solution. The resulting mixture was reacted overnight at room temperature, and then dialyzed with distilled water for 3 days to remove residual reagents. After the dialysis, the solution was freeze-dried. Thereby, an amine group was introduced into the hyaluronic acid.

(2) Synthesis of Hyaluronic Acid Complex

An MES buffer (1% w/v) in which the modified hyaluronic acid prepared in (1) was dissolved, and methanol (1% w/v) in which PBA was dissolved were mixed. EDC and sulfo-NHS were added to the mixed solution. After a reaction, the mixture was loaded into a dialysis bag (MWCO=3,500), and then dialyzed with a mixed solution of water and methanol for 4 days. After the dialysis, the solution was freeze-dried.

Figure 2:
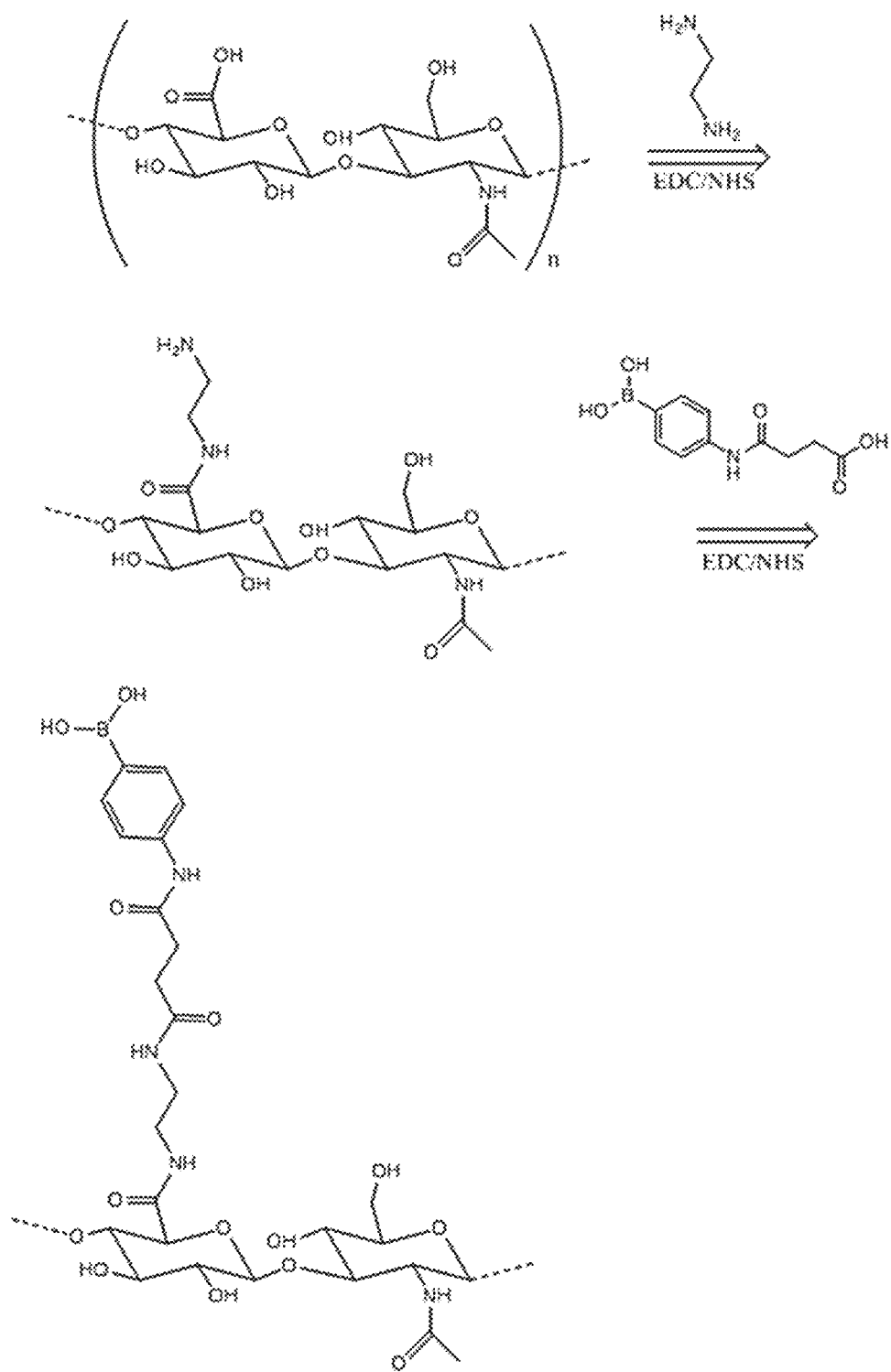
FIG. 2 shows a process of synthesizing a hyaluronic acid complex through an EDC/NHS reaction and a structure of the hyaluronic acid complex.

FIG. 2 is a schematic diagram showing a binding reaction of a boronic acid compound to hyaluronic acid.

Ethylenediamine was chemically bound to a carboxyl group of HA by carbodiimide chemistry. PBA was chemically introduced into the hyaluronate-ethylenediamine conjugate.

(3) Synthesis of Glucose-Responsive Nanoparticles (HA-PBA Nanoparticles)

The hyaluronic acid complex prepared in (2) was dissolved in distilled water.

As the concentration of the hyaluronic acid complex, a concentration of 0.08 mg/mL or more was used to spontaneously assemble the hyaluronic acid complex to form glucose-responsive nanoparticles (HA-PBA nanoparticles).

Hereinafter, the HA-PBA nanoparticles having a degree of substitution of 20 are referred to as HA-PBA 20 (HAPBA 20), and the HA-PBA nanoparticles having a degree of substitution of 33 are referred to as HA-PBA 33 (HAPBA 33), depending on the degree of substitution (DS) of PBA conjugated to HA in the HA-PBA nanoparticles.

Experimental Example 1

Confirmation of Formation of Hyaluronic Acid Complex

The formation of the hyaluronic acid complex was confirmed using FTIR and 1H-NMR.

The conjugation of PBA to HA was measured at a range of 500 to 2,200 cm-1 using FTIR spectroscopy (Nicolet 6700, Thermo Scientific).

FIG. 3 shows the results of FTIR analysis of the hyaluronic acid complex. In FIG. 3 show the results of analysis of (a) the HA, (b) the hyaluronate-ethylenediamine conjugate, and (c) the hyaluronic acid complex.

As shown in FIG. 3, (b) and (c), it can be seen that the C=O stretch peaks at 1,730 cm-1 decreased because the carboxyl group of HA was consumed by the conjugation. The absorption peak at 1,560 cm-1 represents an N—H bond corresponding to the formation of an amine bond.

The conjugation of PBA to HA was also able to be confirmed by 1H-NMR spectroscopy.

FIG. 4 shows the results of 1H-NMR analysis of (a) the hyaluronic acid, (b) the boronic acid compound, and (c) the hyaluronic acid complex.

The peak for the acetyl protons of HA was observed at 1.9 ppm. The peaks for the saccharide protons were observed at 3.5 to 3.9 ppm. The peaks at 7.4 to 7.8 ppm represent HA-PBA conjugation. The results showed that PBA was successfully conjugated to HA.

The DS values may be adjusted by varying the ratio of the boronic acid compound conjugated to the hyaluronic acid. The actual DS values were in a range of 20 to 33.

Experimental Example 2

Confirmation of Size and Morphology of Nanoparticles

The degree of substitution (DS) of PBA conjugated to HA was analyzed using an Elemental Analyzer (FLASHEA 1112). The particle diameter of the HA-PBA nanoparticles (1 mg/mL) was measured using dynamic light scattering (DLS; Nano ZS, Malvern Instruments). Also, the morphology of the HA-PBA nanoparticles was observed by atomic force microscopy (AFM). The HA-PBA nanoparticles were placed on a surface of a silicon water, and dried for 2 hours before capturing images.

The results of measurements are listed in the following Table 1.

TABLE 1

|  | HA-PBA 20 | HA-PBA 33 |
| --- | --- | --- |
| Theoretical DS | 50 | 100 |
| Actual DS | 20 | 33 |
| Diameter (nm) | 257 ± 54 | 225 ± 110 |

The self-assembled HA-PBA nanoparticles were prepared under aqueous conditions. The average diameters of the nanoparticles were 257 nm and 223 nm, respectively, when the nanoparticles had degrees of substitution (DS) of 20 and 33.

FIG. 5 shows an AFM image for identifying the morphology of the synthesized nanoparticles.

As shown in FIG. 5, it can be seen that the HA-PBA nanoparticles had a spherical shape.

Experimental Example 3

Measurement of Critical Micelle Concentration (CMC) of Hyaluronic Acid Complex (1) Method The critical micelle concentration (CMC) of the hyaluronic acid complex was analyzed using fluorescence spectroscopy.

Pyrene was dissolved in tetrahydrofuran (THF), diluted with distilled water (12×10-7 M), and then added to hyaluronic acid complex solutions having different concentrations. The concentration of the hyaluronic acid complex solution was in a range of 1.0×10-5 mg/mL to 1.0×10 mg/mL. To obtain the pyrene excitation spectra, the slit widths for emission and excitation were adjusted to 5 nm and 2.5 nm, respectively. The CMC was determined from a plot of the intensity ratio in a wavelength range of 390 to 378 nm depending on the concentration of the hyaluronic acid complex.

Also, changes in size and fluorescence intensity of the nanoparticles were measured in the presence of glucose (0 to 10 mg/mL) to determine the glucose responsiveness of the HA-PBA nanoparticles.

(2) Results

FIG. 6 shows the results of measuring a critical micelle concentration (CMC) of the hyaluronic acid complex.

In the present invention, the CMC was calculated by measuring the intensity ratio (1390/1378) of pyrene collected into the HA-PBA nanoparticles. Pyrene has different photophysical characteristics depending on the ambient hydrophilic and hydrophobic environments.

To determine the minimum concentration at which the hyaluronic acid complex formed micelles, a value of the fluorescence intensity ratio according to the concentration of the hyaluronic acid complex was measured. The results of measurement showed that the CMC value was 0.08 mg/mL when the nanoparticles had a degree of substitution of 20. That is, the hyaluronic acid complex was assembled at a concentration of 0.08 mg/mL or more to form micelles, that is, nanoparticles (FIG. 6(A)).

Also, the excitation spectra of the HA-PBA nanoparticles (1 mg/mL) having a degree of substitution of 20 were measured under various glucose concentration conditions.

The measurements were carried out at varying glucose concentrations ranging from 1.0×10-5 mg/mL to 1.0×10 mg/mL. The fluorescence intensity ratio of pyrene to the glucose-responsive HA-PBA nanoparticles decreased at 1.48 mg/mL. This suggests that a self-assembled structure was disrupted due to interactions between PBA conjugated to HA and diols in glucose. That is, it can be seen that the micelle morphology of the nanoparticles was disrupted at a concentration of greater than 1.48 mg/mL (FIG. 6(B)).

Also, the CMC was measured in the presence of xylose to check whether the synthesized nanoparticles were specifically responsive to other monosaccharides.

FIG. 7 shows the results of measuring the pyrene excitation spectra of the HA-PBA nanoparticles (1 mg/mL) in the presence of a varying concentration of xylose.

Xylose did not have an influence on the stability of the HA-PBA nanoparticles. This indicates that the HA-PBA nanoparticles may maintain their stability and structure at a normal glucose concentration (1 mg/mL). Also, this indicates that the system of the present invention may not be changed by other monosaccharides.

Generally, the average blood glucose concentration is 1 mg/mL. For the hyaluronic acid complex of the present invention, the nanoparticles (having a self-assembled structure) were disrupted at a glucose concentration of greater than 1.48 mg/mL. Therefore, hereinafter, glucose present at a concentration of less than approximately 1.5 mg/mL is referred to as low glucose, and glucose present at a concentration of 1.5 mg/mL or more is referred to as high glucose. In the examples, the low glucose refers to 1 mg/mL of glucose, and the high glucose refers to 4.5 mg/mL of glucose.

Experimental Example 4

Evaluation of Toxicity of Nanoparticles (1) Method

To check whether the materials such as hyaluronic acid and a boronic acid compound exhibit toxicity, the cytotoxicity (cell viability) was evaluated for hepatocellular carcinoma (HepG2) cells and colorectal carcinoma (HCT 116) cells using MTT analysis.

The HepG2 and HCT 116 cells were respectively cultured in DMEM (10% FBS, 1% penicillin/streptomycin) and RPMI 1640 medium (10% FBS, 1% penicillin/streptomycin), and used for cytotoxicity tests.

The cells were seeded in 96-well tissue culture plates at a density of 5×103 cells/well, treated with the HA-PBA nanoparticles (concentration: 0.1 or 0.5 mg/mL) having a degree of substitution of 20, and then incubated at 37° C. for 24 hours under 5% CO2 conditions.

After the incubation, the cells were washed three times with PBS, and treated with 1 mg/mL of an MTT solution. After 4 hours of the incubation, formazan crystals were dissolved in DMSO, and the optical densities at 540 nm were measured using a UV/VIS spectrophotometer (SpectraMax M2e, Molecular Devices).

(2) Results

In vitro cytotoxicity of the HepG2 and HCT 116 cells treated with a varying concentration of the HA-PBA nanoparticles (having a degree of substitution of 20) dispersed in the high glucose medium (glucose concentration: 4.5 mg/mL) was evaluated. Upon the toxicity evaluation, the MTT analysis was performed under high glucose conditions because the structure of the HA-PBA nanoparticles was not maintained at the high glucose concentration.

Figure 8:
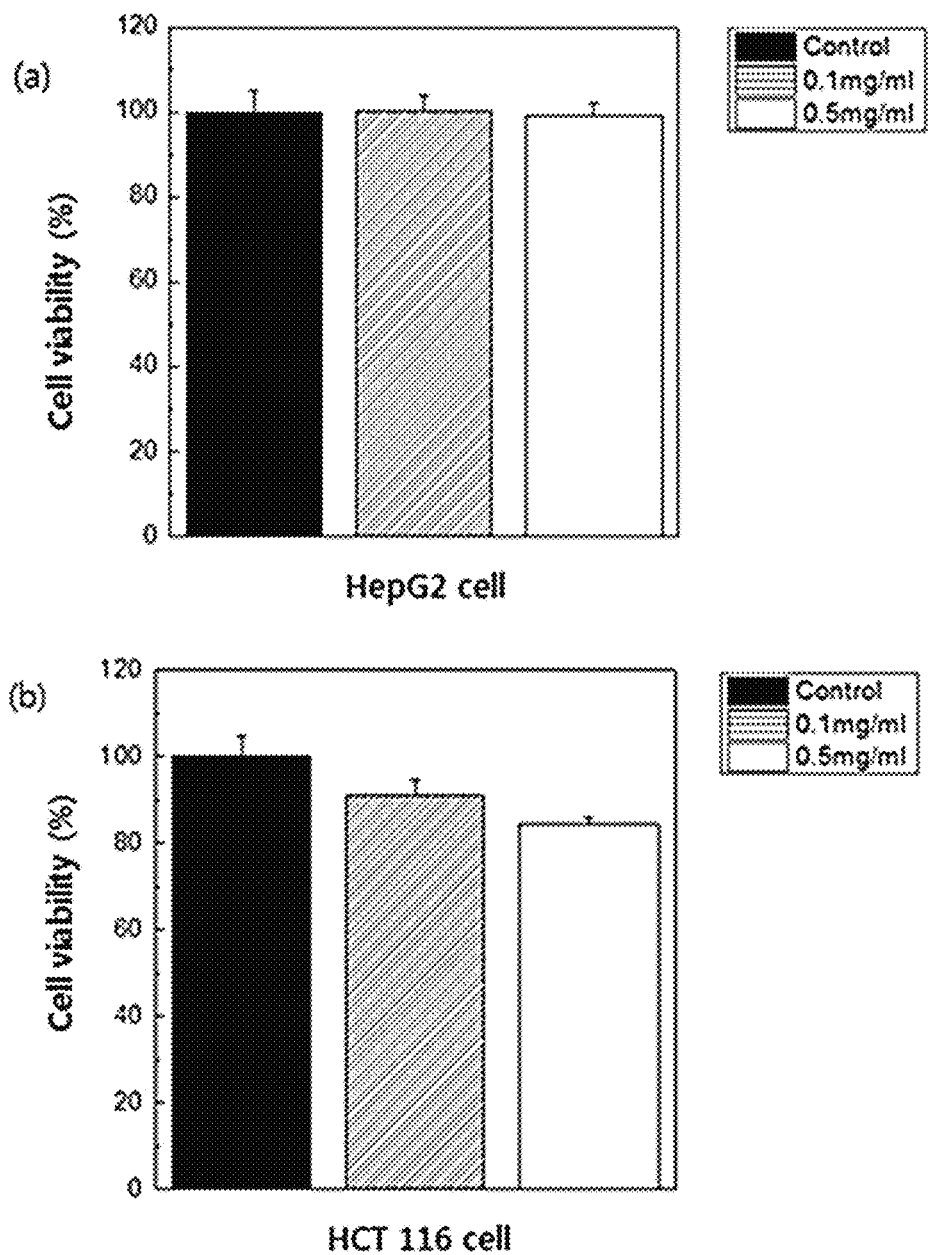
FIG. 8 shows the results of measuring in vitro cytotoxicity of the glucose-responsive nanoparticles with respect to (A) HepG2 cells and (B) HCT 116 cells.

FIG. 8 shows the results of measuring in vitro cytotoxicity of the HA-PBA nanoparticles with respect to (A) HepG2 cells and (B) HCT 116 cells.

As shown in FIG. 8, it was revealed that the viability of the cells was hardly changed in the presence of the HA-PBA nanoparticles at concentrations of 0.1 mg/mL and 0.5 mg/mL. From these facts, it can be seen that the nanoparticles exhibited low toxicity.

Experimental Example 5

Verification of Effect of Nanoparticles on Glycolysis Inhibition (In Vitro)

(1) Method

The intracellular ATP content and lactate production by glycolysis were examined in vitro.

HepG2 cells (5×105 cells/well) were cultured for 24 hours in a 6-well tissue culture plate. The cultured cells were treated for 12 hours with the HA-PBA nanoparticles (1 mg/mL) having a degree of substitution of 20 or 2-deoxy-D-glucose (2DG) (0.25 mg/mL), which was dispersed in a low glucose medium.

The 2-deoxy-D-glucose was used as a glycolytic inhibitor. The ATP content was measured using an ATP Colorimetric/Fluorometric Assay Kit (Biovision). Lactate secretion was quantified using an EnzyChrom™ L-Lactate Assay Kit (Bioassay). In cell fate, an effect of the HA-PBA nanoparticles on the inhibition of glycolysis was examined using a flow cytometer (BD FACS Caliber).

Briefly, the HepG2 cells were treated with the HA-PBA nanoparticles or 2DG for 12 hours. An Annexin-V-FITC antibody and propidium iodide (PI) were used as markers for apoptotic and necrotic cell death. The HepG2 cells were seeded in a 24-well tissue culture plate at a density of 1×104 cells/well, and incubated at 37° C. for 24 hours under 5% CO2 conditions. The cells were washed with PBS, and treated for 8 hours with a low or high glucose medium including the HA-PBA nanoparticles (1 mg/mL) having a degree of substitution of 20. Also, prior to treatment with the HA-PBA nanoparticles, the cells were pretreated with a hyaluronate (2.5 mg/mL) dissolved in a low glucose medium. The medium was replaced with a fresh medium daily. At a predetermined point of time, the cells were treated with EZ-Cytox for 2 hours, and the optical density at 450 nm was measured using a UV/VIS spectrophotometer. The growth rate of the cells was calculated from a change in the number of the cells in 3 days of incubation.

(2) Results

To examine an effect of the HA-PBA nanoparticles on the inhibition of glycolysis in the HepG2 cells, changes in the ATP and lactate contents were quantified. When the HA-PBA nanoparticles were delivered to the HepG2 cells, the intracellular ATP content decreased to as low as the 2-deoxy-D-glucose (2DG) (see FIG. 9(B)). 2DG is generally used as a glycolytic inhibitor because the 2DG blocks a pathway from glucose to glucose-6-PO4 to inhibit ATP production in glycolysis (see FIG. 9(A)).

Also, FIG. 10 shows in vitro secretion of lactate in the HepG2 cells. As shown in FIG. 10, the secretion of lactate decreased to as low as the 2-deoxy-D-glucose (2DG) when the HA-PBA nanoparticles were delivered to the HepG2 cells.

These findings showed that the HA-PBA nanoparticles were effective in inhibiting aerobic glycolysis.

An effect of the inhibition of glycolysis by the HA-PBA nanoparticles on apoptotic and necrotic cell death was examined using flow cytometric analysis.

Annexin V is a Ca2+-dependent phospholipid-binding protein having an affinity to phosphatidylserine. Phosphatidylserine is used as a sensitive probe exposed to outer leaflets of cell membranes, and used to detect apoptotic cells. On the other hand, propidium iodide is used to stain only DNA in leaky necrotic cells. The results in dot charts and the percentages of intensities are shown in FIG. 11.

More apoptotic cells were found in the HA-PBA nanoparticle-treated group, compared to the control and the 2DG-treated group. The ratio of apoptotic/in-late apoptotic HepG2 cells were 6.76%/5.77% and 18.81%/4.65% in the case of the control and the 2DG-treated group. However, the numbers of apoptotic and in-late apoptotic HepG2 cells were 22.83% and 19.55% in the case of the HA-PBA nanoparticles-treated group. This indicated that the HA-PBA nanoparticles suppressed glycolysis, and also induced apoptosis in the hepatocellular carcinoma cells.

To check the inhibition of cell growth by the HA-PBA nanoparticles, intracellular entry of the nanoparticles and an effect of the nanoparticles on the inhibition of growth of HepG2 cells was evaluated. The cells were treated with the HA-PBA nanoparticles for 8 hours, and incubated for 3 days in a low glucose medium or a high glucose medium. Also, the cells were pretreated soluble HA dissolved in the low glucose medium to test whether the internalization of the HA-PBA nanoparticles was mediated by a CD44 receptor.

FIG. 12 show the results of growth of HepG2 cells treated daily with a low glucose medium, a high glucose medium, a low glucose medium including the HA-PBA nanoparticles, a high glucose medium including the HA-PBA nanoparticles, and a HA-pretreated low glucose medium including the HA-PBA nanoparticles.

The cell growth rate increased in the cells treated with the high glucose medium. This is because an inhibitory effect on cell growth was not observed because the HA-PBA nanoparticles are disrupted under the high glucose conditions. However, the cell growth rate decreased in the low glucose medium. It was expected that the shape of the nanoparticles was maintained under the low glucose conditions, and the nanoparticles induced the inhibition of aerobic glycolysis.

When the cells were treated with the HA-PBA nanoparticles in the high glucose medium, the cell growth rate was not hampered by the nanoparticles when the CD44-positive HepG2 cells were pretreated with soluble HA to block the CD 44 receptor. The results showed that the structure of the HA-PBA nanoparticles was maintained in a medium with a normal glucose level (a low glucose level), and the HA-PBA nanoparticles were able to bind to the CD44 receptor in the cells suppressing the glycolysis in cancer cells.

Experimental Example 6

Cellular Entry (In Vitro)

(1) Method

The receptor-mediated endocytosis of the glucose-responsive HA-PBA nanoparticles in HepG2 and NIH3T3 cells was determined using confocal laser scanning microscopy (Olympus, FV1200).

First, Cy5.5-conjugated HA-PBA nanoparticles (having a degree of substitution of 20) were prepared.

The HA-PBA nanoparticles and Cy5.5-NHS were dissolved in distilled water (Cy5.5/polymer=0.01 w/w). The mixture was reacted overnight (while avoiding light). The solution was dialyzed for 4 days, and freeze-dried.

The HepG2 and NIH3T3 cells were seeded in a 12-well non-tissue culture plate at a density of 1×104 cells/well, and incubated for 24 hours. The cells were treated with the Cy5.5-conjugated HA-PBA nanoparticles (1 mg/mL). After 4 hours, the medium was removed, and the cells were washed three times with PBS. The cells were fixed with 4% formaldehyde for 10 minutes, and then mounted on a slide glass using a mounting medium including 4',6'-diamino-2-phenylindole (DAPI, Vectashield).

To evaluate the CD44 receptor-mediated endocytosis, the cells were pretreated for 2 hours with a hyaluronate solution (2.5 mg/mL) dissolved in a low glucose medium (2.5 mg/mL) prior to addition of the nanoparticles.

The Cy5.5-conjugated HA-PBA nanoparticles and LysoTracker Green DND-26 (Invitrogen) were used to monitor the intracellular entry of the glucose-responsive HA-PBA nanoparticles in the HepG2 and NIH3T3 cells.

The HepG2 cells or NIH3T3 cells were seeded in a 12-well non-tissue culture plate at a density of 1×104 cells/well, and incubated for 24 hours before use. The Cy5.5-conjugated HA-PBA nanoparticles (1 mg/mL) were added to the plate, and incubated for 4 hours. Thereafter, LysoTracker Green DND-26 (100 nM) was added to the plate, and the cells were incubated for 2 hours. The medium was removed, and the cells were washed three times with PBS. The cells were fixed with 4% formaldehyde for 10 minutes, and then mounted on a slide glass using a mounting medium including 4',6'-diamino-2-phenylindole (DAPI, Vectashield). Then, the shape of the nanoparticles was observed using fluorescence microscopy (Nikon, TE2000-E).

(2) Results

The receptor-mediated endocytosis of the HA-PBA nanoparticles into the cells was examined.

The CD44-positive cells (HepG2) or CD44-negative cells (NIH3T3) were treated with Cy5.5-conjugated HA-PBA nanoparticles to examine CD44-dependent endocytosis.

FIG. 13 shows a confocal microscopy image of (A) HepG2 cells and (B) NIH3T3 cells treated with Cy5.5-conjugated HA-PBA nanoparticles in the low glucose medium or the high glucose medium.

As shown in FIG. 13, it can be seen that the signal of Cy5.5 was highly detected in the HepG2 cells incubated in the low glucose medium, compared to the soluble HA-treated group. On the other hand, no significant signal was observed in the HepG2 and CD44-negative NIH3T3 cells incubated in the high glucose medium. The results suggest that the HA-PBA nanoparticles are not captured by the CD44-negative cells under the high glucose conditions. Also, the pretreatment of the cells with soluble HA blocked the CD44 receptor in the cells, resulting in reduced cellular uptake.

The HA-PBA nanoparticles had excellent binding affinity to the CD44-positive cells, and the receptor-mediated endocytosis is capable of being a primary cell uptake pathway.

Also, LysoTracker Green DND-26 was used to track the intracellular entry of the HA-PBA nanoparticles.

The LysoTracker Green has high selectivity to acidic organelles, and is often used for tracking. As can be seen from the fluorescence microscopy, it was revealed that the signal of the Cy5.5-conjugated HA-PBA nanoparticles was highly detected in the HepG2 cells incubated in the low glucose conditions, compared to the cells incubated in the high glucose conditions or the CD44-negative cells. This indicates that the HA-PBA nanoparticles are introduced into the HepG2 cells through the endocytic pathway.

Example 7

Tumor-Targeting Ability (In Vivo)

(1) Method

To check a biodistribution of the HA-PBA nanoparticles in a tumor-bearing mouse model, an anesthetic drug (Zoletil (35 mg/kg)/Rompun (2 mg/kg)) was injected into athymic nude mice (20 g, 5 week-old, Orient lab animals), and a HepG2 cell suspension (5×106 cells/mouse) was inoculated into the left sides of the mice.

After 14 days, Cy5.5-conjugated HA-PBA nanoparticles were intravenously injected into the caudal veins of the mice at a dose of 10 mg/kg. At 24 hours after injection, the mice were sacrificed, and major organs and tumors were extracted, and observed using a Kodak image station (Kodak Image Station 4000 MM, Kodak) (n=3)

(2) Results

FIG. 15 shows (A) an in vivo biodistribution of the HA-PBA nanoparticles and (B) the results of quantifying tumor specificity in a tumor-bearing mouse model.

The strongest signal of the Cy5.5-conjugated HA-PBA nanoparticles was detected in tumor sites, compared to normal organs. It was expected that the signal was accumulated around the tumor sites due to the receptor-mediated endocytosis as well as the EPR (enhanced permeation and retention) effect. The signal was detected in the liver due to the intracellular entry of the HA-PBA nanoparticles into liver sinusoidal endothelial cells expressing a hyaluronan receptor for endocytosis (HARE) and a reticuloendothelial system (RES). The results show that the HA-PBA nanoparticles are accumulated at the tumor sites to exhibit a potential for treating cancer.

Experimental Example 8

Evaluation of In Vivo Therapeutic Effect
(Inhibitory Effect on Liver Cancer Growth)

(1) Method

To evaluate a therapeutic effect of the HA-PBA nanoparticles, the tumor-bearing mouse model of Experimental Example 7 was prepared.

The HA-PBA nanoparticles (20 mg kg), paclitaxel (10 mg/kg), and PBS were intravenously injected into the caudal veins of the tumor-bearing mice (injected 5 times for a week). Changes in tumor volume were monitored for 2 weeks (n=7). Tumor tissues were extracted from the mice, and embedded into an optimal cutting temperature (OCT) compound. The tumor tissues were cut into sections (12 μm thick), and stained with hematoxylin and eosin (H&E) and a DeadEnd™ colorimetric TUNEL system (Promega, USA).

(2) Results

When the tumor volumes of the mice reached approximately 90 mm3, the HA-PBA nanoparticles, paclitaxel, and PBS were injected into the mice.

FIG. 16 shows (A) the results of in vivo therapeutic efficacy of the HA-PBA nanoparticles and (B) the results of H&E and TUNEL staining of tumor tissues.

The tumor volumes and weights were monitored for 17 days. As a result, it was revealed that the groups treated with the HA-PBA nanoparticles and the paclitaxel had an inhibited tumor growth rate, compared to the PBS-treated group. No weight loss was observed in all the groups.

The results show that the HA-PBA nanoparticles have no side effects at undesired sites and an excellent therapeutic effect. The enhanced therapeutic efficacy is due to the tumor-targeting ability of the HA-PBA nanoparticles.

Also, histological images of the tumor tissues show that the HA-PBA nanoparticles exhibit excellent therapeutic efficacy. Many apoptotic cells were observed in the mice treated with the HA-PBA nanoparticles. Such enhanced therapeutic efficacy shows that the glucose-responsive nanoparticles suppress the growth of the tumor cells by blocking the glycolysis at the tumor sites.

INDUSTRIAL APPLICABILITY

The present invention provides a composition for diagnosing or treating liver cancer or simultaneously diagnosing and treating liver cancer. When the nanoparticles or composition of the present invention is used, cancer can be diagnosed and treated using a cancer cell-specific biological mechanism without using conventional contrast agents and anticancer agents having toxicity problems.

The invention claimed is:

1. A hyaluronic acid complex comprising a hyaluronic acid-boronic acid repeating unit in which a boronic acid compound is bound to a carboxyl group of a repeating unit represented by the following Formula 1

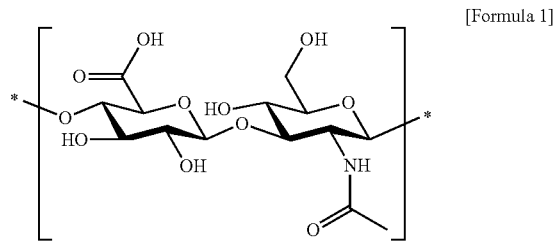

[Formula 1]

wherein the boronic acid compound in the hyaluronic acid-boronic acid repeating unit is bound to a hyaluronic acid repeating unit via an amide bond by means of a diamine compound serving as a linker, and wherein the diamide compound is ethylenediamine, butylenediamine, hexamethylenediamine, pentaethylenehexamine, or 1,5-diamino-2-methylpentane.

2. The hyaluronic acid complex of claim 1, wherein a content of the hyaluronic acid-boronic acid repeating unit is in a range of 15 to 55 parts by mol, based on 100 parts by mol of the hyaluronic acid complex.

3. The hyaluronic acid complex of claim 1, wherein the boronic acid compound is phenylboronic acid.

4. The hyaluronic acid complex of claim 3, wherein the phenylboronic acid comprises one or more selected from the group consisting of N-(4-phenylboronic) succinamic acid, 3-carboxybenzenebenzoic acid, 4-carboxypyridine-3-benzoic acid, and (3-aminomethylphenyl) benzoic acid chloride.

5. The hyaluronic acid complex of claim 1, wherein the hyaluronic acid complex comprises the hyaluronic acid repeating unit represented by Formula 1 together with the hyaluronic acid-boronic acid repeating unit.

6. A plurality of glucose-responsive nanoparticles that are spherical particles having a hydrophobic core, wherein the hyaluronic acid complex defined in claim 1 is self-aggregated to form the spherical particles.

7. The glucose-responsive nanoparticles of claim 6, wherein the nanoparticles have an average diameter of 200 nm to 400 nm.

8. The glucose-responsive nanoparticles of claim 6, further comprising a fluorescent signal material with which spherical particles are chemically labeled or which is physically loaded into a hydrophobic core.

9. The glucose-responsive nanoparticles of claim 8, wherein the fluorescent signal material is chlorine 6 (Ce6) or cyanine 5.5 (Cy5.5).

10. A pharmaceutical composition for diagnosing or treating liver cancer, comprising the glucose-responsive nanoparticles defined in claim 6.

11. The pharmaceutical composition of claim 10, which inhibits aerobic glycolytic metabolism of cancer cells by using glucose responsivity.

\* \* \* \* \*